US00PP15839P2

(12) United States Plant Patent
Miedema-Jorna

(10) Patent No.: US PP15,839 P2
(45) Date of Patent: Jul. 5, 2005

(54) *PETUNIA* PLANT NAMED 'FORT RED'

(50) Latin Name: *Petunia×hybrida*
Varietal Denomination: Fort Red

(75) Inventor: Anita Miedema-Jorna, De Lier (NL)

(73) Assignee: Fides Goldstock Breeding B.V., DeLier (NL)

( * ) Notice: Subject to any disclaimer, the term of this patent is extended or adjusted under 35 U.S.C. 154(b) by 0 days.

(21) Appl. No.: 10/924,023

(22) Filed: Aug. 23, 2004

(51) Int. Cl.[7] ..... A01H 5/00
(52) U.S. Cl. ..... Plt./356
(58) Field of Search ..... Plt./356

(56) References Cited

U.S. PATENT DOCUMENTS

PP14,243 P2 * 10/2003 Hanes ..... Plt./356
PP14,276 P2 * 11/2003 Hanes ..... Plt./356
PP14,322 P2 * 11/2003 Hanes ..... Plt./356
PP14,998 P2 * 7/2004 Brown ..... Plt./356

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Petunia* plant named 'Fort Red', characterized by its upright and outwardly spreading and mounded plant habit; freely branching habit; freely flowering habit; large single flowers that are red in color; and good garden performance.

2 Drawing Sheets

Botanical designation: *Petunia×hybrida.*
Variety denomination: 'Fort Red'.

BACKGROUND OF THE INVENTION

The present Invention relates to a new and distinct cultivar of *Petunia* plant, botanically known as *Petunia×hybrida,* and hereinafter referred to by the cultivar name Fort Red.

The new *Petunia* is a product of a planned breeding program conducted by the Inventor in De Lier, The Netherlands. The objective of the breeding program is to create new freely flowering *Petunias* with an outwardly spreading plant habit and attractive leaf and flower coloration.

The new *Petunia* originated from a cross-pollination made by the Inventor in 2002 of a proprietary seedling selection of *Petunia×hybrida* identified as code number 0390, not patented, as the female, or seed, parent with a proprietary seedling selection of *Petunia×hybrida* identified as code number 408, not patented, as the male, or pollen, parent. The new *Petunia* was selected as a single plant from the resulting progeny of the stated cross-pollination in a controlled environment in De Lier, The Netherlands.

Asexual reproduction of the new cultivar by terminal vegetative cuttings since 2003, in De Lier, The Netherlands has shown that the unique features of this new *Petunia* are stable and reproduced true to type in successive generations.

SUMMARY OF THE INVENTION

Plants of the cultivar Fort Red have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Fort Red'. These characteristics in combination distinguish 'Fort Red' as a new and distinct cultivar.

1. Upright and outwardly spreading and mounded plant habit.
2. Freely branching habit.

3. Freely flowering habit.
4. Large single flowers that are red in color.
5. Good garden performance.

In side-by-side comparisons conducted in De Lier, The Netherlands, plants of the new *Petunia* differed from plants of the female parent selection in the following characteristics:

1. Plants of the new *Petunia* were more vigorous than plants of the female parent selection.
2. Plants of the new *Petunia* flowered earlier than plants of the female parent selection.

In side-by-side comparisons conducted in De Lier, The Netherlands, plants of the new *Petunia* differed from plants of the male parent selection in the following characteristics:

1. Plants of the new *Petunia* were more upright than and not as cascading as plants of the male parent selection.
2. Flowers of plants of the new *Petunia* flowered earlier than plants of the male parent selection.

Plants of the new *Petunia* also can be compared to plants of the cultivar Big Red Rising Sun, not patented. In side-by-side comparisons conducted in De Lier, The Netherlands, plants of the new *Petunia* differed from plants of the cultivar Big Red Rising Sun in the following characteristics:

1. Leaves of plants of the new *Petunia* were larger than plants of the cultivar Big Red Rising Sun.
2. Plants of the new *Petunia* were more upright than plants of the cultivar Big Red Rising Sun.
3. Flowers of plants of the new *Petunia* were larger than flowers of plants of the cultivar Big Red Rising Sun.

Plants of the new *Petunia* also can be compared to plants of the cultivar Surfinia Red, not patented. In side-by-side comparisons conducted in De Lier, The Netherlands, plants of the new *Petunia* differed from plants of the cultivar Surfinia Red in the following characteristics:

1. Plants of the new *Petunia* were more upright than plants of the cultivar Surfinia Red.
2. Plants of the new *Petunia* had shorter internodes than plants of the cultivar Surfinia Red.
3. Flowers of plants of the new *Petunia* were more intense red in color than flowers of plants of the cultivar Surfinia Red.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Petunia*.

The photograph on the first sheet comprises a side perspective view of a typical plant of 'Fort Red' grown in a container.

The photograph on the second sheet is a close-up view of typical flowers and leaves of 'Fort Red'.

DETAILED BOTANICAL DESCRIPTION

Plants of the cultivar Fort Red have not been observed under all possible environmental conditions. The phenotype may vary somewhat with variations in environment such as temperature and light intensity, without, however, any variance in genotype. The aforementioned photographs and following observations and measurements describe plants grown in De Lier, The Netherlands, in 10.5 cm containers and under commercial practice in a glass-covered greenhouse during the summer with day and night temperatures ranging from 15 to 18° C. Plants used for the photographs and description were about ten weeks from planting rooted cuttings. In the following description, color references are made to The Royal Horticultural Society Colour Chart, 2001 Edition, except where general terms of ordinary dictionary significance are used.

Botanical classification: *Petunia×hybrida* cultivar Fort Red.

Parentage:

*Female parent.*—Proprietary seedling selection of *Petunia×hybrida* identified as code number 0390, not patented.

*Male parent.*—Proprietary seedling selection of *Petunia×hybrida* identified as code number 408, not patented.

Propagation:

*Type cutting.*—Terminal vegetative cuttings.

*Time to initiate roots.*—Summer: About 5 to 7 days at 19 to 20° C. Winter: About 6 to 8 days at 19 to 20° C.

*Time to develop roots.*—Summer: About 14 to 19 days at 19 to 20° C. Winter: About 14 to 21 days at 19 to 20° C.

*Root description.*—Fine; white in color.

*Rooting habit.*—Freely branching.

Plant description:

*Form.*—Annual flowering plant; indeterminate; upright and outwardly spreading and mounded plant habit. Freely branching habit, about eight lateral branches per plant. Moderately vigorous.

*Plant height.*—About 16 cm.

*Plant diameter (area of spread).*—About 26 cm.

*Lateral branches.*—Length: About 10.5 cm. Diameter: About 4 mm. Internode length: About 1.7 cm. Texture: Densely pubescent; viscid. Strength: Moderately strong. Color: 144A.

*Foliage description.*—Arrangement: Alternate; simple; sessile. Length: About 5.9 cm. Width: About 2.9 cm. Shape: Ovate to elliptic. Apex: Acute. Base: Attenuate. Margin: Entire. Texture, upper and lower surfaces: Densely pubescent; viscid. Venation pattern: Pinnate, arcuate. Color: Developing and fully expanded leaves, upper surface: 137B; venation, 143A to 143B. Developing and fully expanded leaves, lower surface: 138B; venation, 143B to 143C.

Flower description:

*Flower type and habit.*—Single salverform flowers; flowers face mostly upwardly or outward; axillary. Freely flowering habit, about two or three open flowers and about five flower buds per lateral branch at one time. Flowers not fragrant.

*Natural flowering season.*—Long day responsive; long flowering period, spring until frost in the autumn; flowering continuous during this period. Plants start flowering about eight weeks after planting rooted cuttings. Flowers persistent.

*Flower longevity on the plant.*—About five days.

*Flower size.*—Diameter: About 6.6 cm. Depth: About 4.3 cm.

*Flower buds.*—Length: About 2.6 cm. Diameter: About 6 mm. Shape: Narrow oblanceolate. Color: 152C to 152D.

*Petals.*—Quantity/arrangement: Five petals fused in a single whorl, funnelform. Length: About 6.2 cm. Width: About 2.8 cm. Shape: Roughly spatulate. Apex: Retuse. Margin: Entire; undulate. Texture, upper and lower surfaces: Smooth, satiny; tube, densely pubescent. Color: When opening, upper surface: More intense than 46A to 46B. When opening, lower surface: 185D. Fully opened, upper surface: 45B to 46B. Fully opened, lower surface: 185D.

*Sepals.*—Arrangement/appearance: Single whorl of five sepals fused at base, star-shaped. Length: About 2.3 cm. Width: About 5 mm. Shape: Narrowly oblong. Apex: Acute. Margin: Entire. Texture, upper and lower surfaces: Densely pubescent; viscid. Color: Developing sepals, upper surface: 137A. Developing sepals, lower surface: 137B. Fully expanded sepals, upper surface: 137B. Fully expanded sepals, lower surface: 137C.

*Peduncles.*—Length: About 3.4 cm. Width: About 2.5 mm. Angle: About 40° from the stem. Strength: Moderately strong. Texture: Pubescent; viscid. Color: 144A.

*Reproductive organs.*—Stamens: Quantity per flower: About five. Filament length: About 1.8 cm. Filament color: Close to 158C. Anther shape: Broadly reniform. Anther length: About 2 mm. Anther color: 158C. Pollen amount: Moderate. Pollen color: 155A. Pistils: Quantity per flower: One. Pistil length: About 2.3 cm. Style length: About 2.2 cm. Style color: 145C. Stigma shape: Flattened, tri-lobed. Stigma color: 143C. Ovary color: 143B.

*Seed/fruit.*—Seed and/or fruit production has not been observed.

Disease/pest resistance: Plants of the new *Petunia* have not been noted to be resistant to pathogens or pests common to *Petunia*.

Garden performance: Plants of the new *Petunia* have been observed to have good garden performance. Plants of the new *Petunia* have been noted to tolerate rain, wind and temperatures from about 0 to about 35° C.

It is claimed:

1. A new and distinct cultivar of *Petunia* plant named 'Fort Red', as illustrated and described.

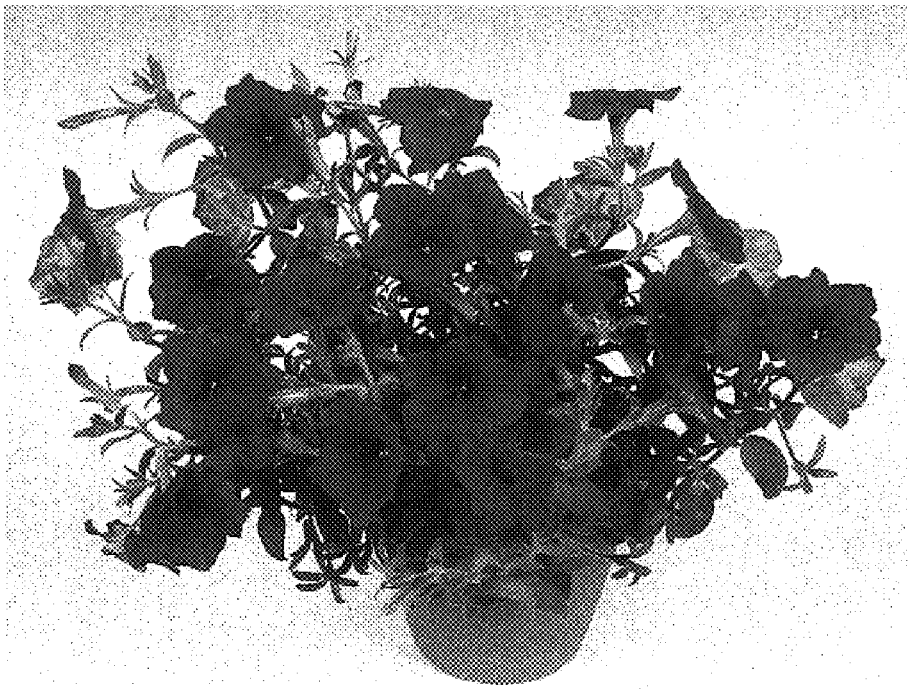

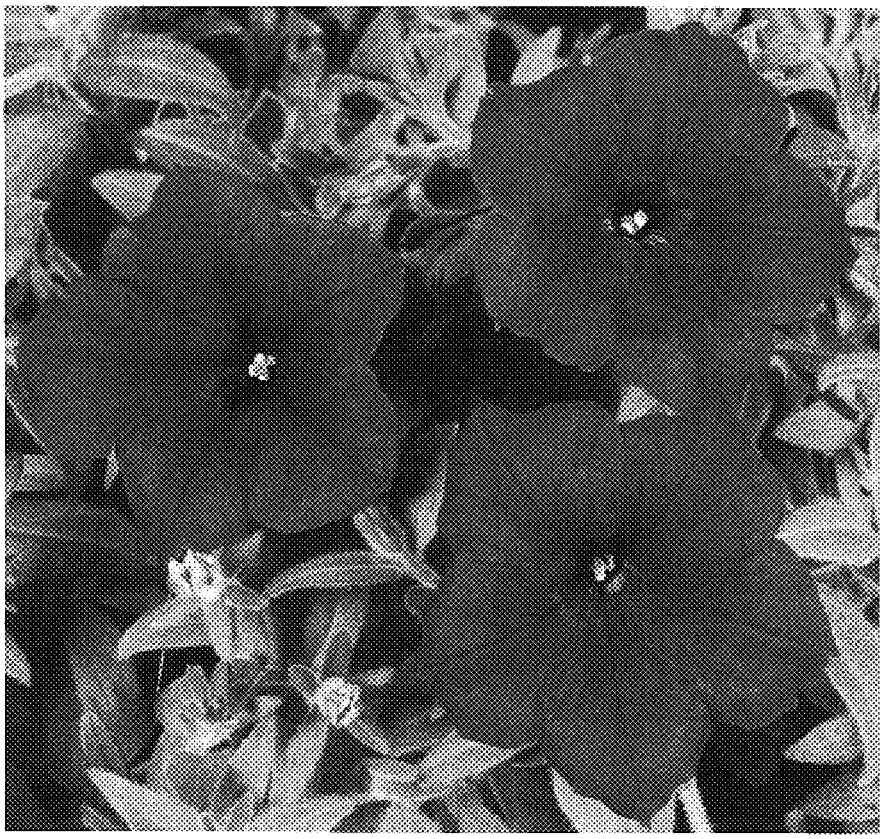

* * * * *